United States Patent
Brehm

(10) Patent No.: US 8,348,953 B2
(45) Date of Patent: Jan. 8, 2013

(54) METHOD AND APPARATUS FOR IMPACTING BONE MATERIAL

(76) Inventor: Peter Brehm, Weisendorf (DE)

( * ) Notice: Subject to any disclaimer, the term of this patent is extended or adjusted under 35 U.S.C. 154(b) by 1247 days.

(21) Appl. No.: 11/972,007

(22) Filed: Jan. 10, 2008

(65) Prior Publication Data

US 2009/0182334 A1  Jul. 16, 2009

(51) Int. Cl.
  *A61B 17/56* (2006.01)
(52) U.S. Cl. ..................... 606/86 R
(58) Field of Classification Search ........... 606/86 R, 606/62, 63, 87–89, 91–95, 99; 623/22.11–23.38
See application file for complete search history.

(56) References Cited

U.S. PATENT DOCUMENTS

| | | | | |
|---|---|---|---|---|
| 4,337,773 A * | 7/1982 | Raftopoulos et al. | ............ | 606/62 |
| 4,878,917 A * | 11/1989 | Kranz et al. | ............ | 623/23.45 |
| 5,078,746 A * | 1/1992 | Garner | ............ | 623/23.48 |
| 5,116,377 A * | 5/1992 | Skripitz et al. | ............ | 623/23.19 |
| 5,385,566 A * | 1/1995 | Ullmark | ............ | 606/95 |
| 5,470,336 A * | 11/1995 | Ling et al. | ............ | 606/105 |
| 5,507,830 A * | 4/1996 | DeMane et al. | ............ | 623/22.42 |
| 5,800,437 A * | 9/1998 | Gustilo et al. | ............ | 606/86 R |
| 5,863,295 A * | 1/1999 | Averill et al. | ............ | 128/898 |
| 5,925,051 A * | 7/1999 | Mikhail | ............ | 606/94 |
| 6,013,080 A * | 1/2000 | Khalili | ............ | 606/86 R |
| 6,015,408 A * | 1/2000 | Pichon et al. | ............ | 606/53 |
| 6,142,998 A * | 11/2000 | Smith et al. | ............ | 606/86 R |
| 6,228,092 B1 * | 5/2001 | Mikhail | ............ | 606/105 |
| 6,589,285 B2 * | 7/2003 | Penenberg | ............ | 623/23.26 |
| 7,141,054 B2 * | 11/2006 | Vandewalle | ............ | 606/92 |
| 7,799,029 B2 * | 9/2010 | Jones | ............ | 606/53 |
| 2002/0065518 A1 * | 5/2002 | Naybour et al. | ............ | 606/86 |
| 2005/0043811 A1 * | 2/2005 | Doubler et al. | ............ | 623/22.42 |

FOREIGN PATENT DOCUMENTS

| | | |
|---|---|---|
| DE | 4320086 A1 | 12/1994 |
| DE | 4320086 C3 | 12/1994 |

OTHER PUBLICATIONS

Wirtz et al., "A modular femoral implant for uncemented stem revision in THR," International Orthopaedics (SICOT) Feb. 16, 2000; 24: pp. 134-138.
Schramm et al., "The Morse Taper Junction in Modular Revision Hip Replacement—A Biomechanical and Retrieval Analysis," Biomedizinische Technik 45; 2000; pp. 105-109.
Mumme et al., "The cement-free modular revision prosthesis MRP-Titanium in clinical follow-up," Z Orthop.; 2004; 142: pp. 314-321.
Mumme et al., "Uncemented Femoral Revision Arthroplasty Using the Modular Revision Prosthesis MRP;TITAN Revision Stem," Urban & Vogal, vol. 18, Issue 1, Feb. 1, 2007; pp. 56-77.
Peter Brehm GmbH, Weisendorf (DE), "IGS—Impacting Grafting System," 2006 brochure.
Peter Brehm GmbH, Weisendorf (DE), "IGS—Impacting Grafting System," Feb. 2007 brochure.

* cited by examiner

*Primary Examiner* — Kevin T Truong
*Assistant Examiner* — Christopher Beccia
(74) *Attorney, Agent, or Firm* — Summa, Additon & Ashe, P.A.

(57) ABSTRACT

An apparatus for impacting bone material comprises an impaction element and a guide element having a bore. The bore has a longitudinal axis. The impaction tool is connected to the guide element, and is provided at a predetermined distance to the bore in a direction substantially perpendicular to the longitudinal axis of the bore. A guide rod may be connected to a medical device and can be inserted into the bore. Thus, the apparatus may be guided into a cavity adjacent the medical device for impacting bone material inserted into the cavity.

35 Claims, 5 Drawing Sheets

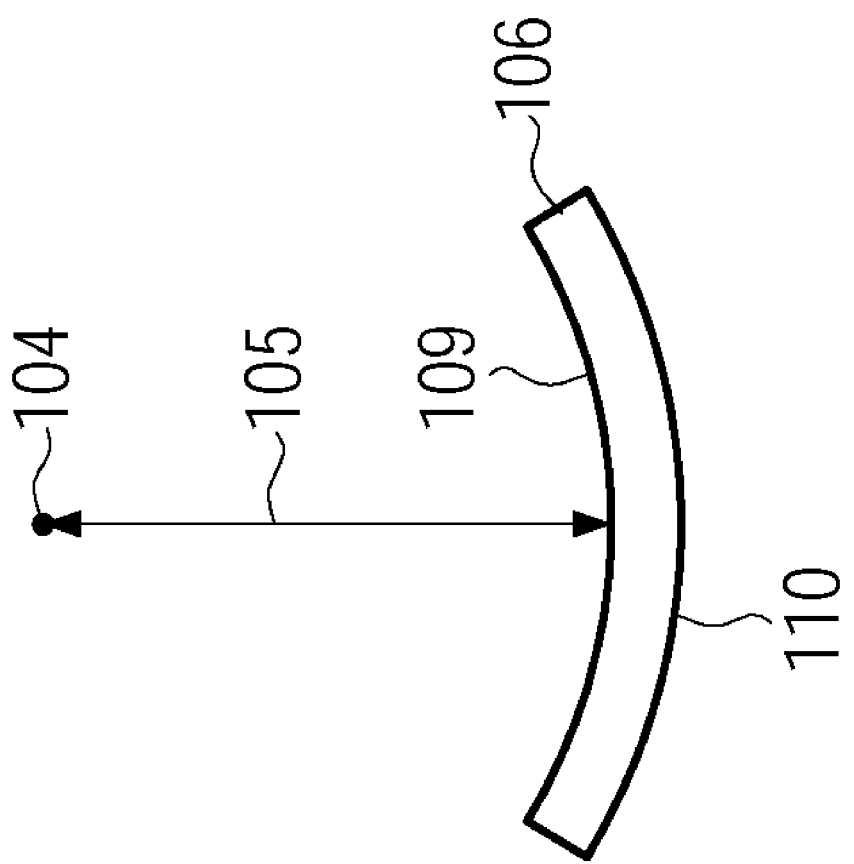

METHOD AND APPARATUS FOR IMPACTING BONE MATERIAL

FIELD OF THE INVENTION

The present invention generally relates to the field of endoprostheses, in particular to an apparatus for impacting bone material, an impaction tool, a method of impacting bone material and a modular system for providing a hip joint endoprosthesis.

BACKGROUND

Hip joint endoprostheses may help to significantly improve the quality of life of patients whose natural hip joint has been damaged by attrition or disease. In the course of time, however, a loosening of the hip joint endoprosthesis may occur, which may necessitate a replacement of the hip joint endoprosthesis by a new hip joint endoprosthesis. In the context of hip joint endoprosthesis loosening, extensive periprosthetic osteolysis is frequently observed. This may make a sufficiently stable anchoring of the new hip joint endoprosthesis difficult, in particular in cases of metaphyseal bone defect.

A revision endoprosthesis according to the state of the art is disclosed, for example, in DE 43 20 086 A1 and in DE 43 20 086 C3. The revision endoprosthesis comprises a stem which may be inserted into the patient's femur, an extension section which may be attached to the stem and a joint ball section which may be attached to the extension section or, alternatively, to the stem. The joint ball section comprises a joint ball attached thereto which can be inserted into an artificial joint socket fixed to the patient's pelvic bone.

The stem of a revision endoprosthesis may be adapted for uncemented diaphyseal anchorage and bridging of the damaged metaphyseal bone bed. Thus, a significant amount of mechanical load may be exhibited to the diaphysis of the femur, leading to a reduced mechanical load in the damaged metaphysis. In situations without metaphyseal defect augmentation and for large diameter stems, this may entail an insufficient mechanical load of the metaphysis and a subsequent atrophy.

To reduce this problem, it has been proposed to fill metaphyseal defects with autogenous and/or allogenic bone material and to impact the bone material. Thus, bone regeneration with corresponding bone remodeling processes and firm integration of the revision endoprosthesis may be obtained.

To introduce bone material into the metaphyseal defects and to impact the bone material, in methods of implanting a revision endoprosthesis according to the state of the art tools such as, for example, surgical chisels or other blunt objects are used.

A problem of the methods according to the state of the art for introducing and impacting bone material into metaphyseal defects is that it may be difficult to introduce a surgical chisel or other blunt object into the metaphyseal defect.

Another problem of the methods according to the state of the art for introducing and impacting bone material in metaphyseal defects is that metaphyseal defects may be insufficiently filled with bone material, which may lead to a formation of cavities between the revision endoprosthesis and the femur. The presence of the cavities may lead to an insufficient anchorage of the revision endoprosthesis in the femur.

Hence, there is a need for an apparatus for impacting bone material, an impaction tool for impacting bone material, a method of impacting bone material and a modular system for providing a hip joint endoprosthesis which may help to overcome some or all of these problems.

SUMMARY

According to an illustrative embodiment, an apparatus for impacting bone material comprises an impaction tool and a guide element having a bore. The bore has a longitudinal axis. The impaction tool is connected to the guide element, and is provided at a predetermined distance to the bore in a direction substantially perpendicular to the longitudinal axis of the bore.

According to another illustrative embodiment, an apparatus for impacting bone material comprises an impaction tool, a guide rod and a guide element. The guide rod is fixable to a medical device. The medical device is insertable into a bone of a patient. The guide element is movable along the guide rod in a longitudinal direction of the guide rod. The impaction tool is connected to the guide element and is provided at a predetermined distance to the guide rod in a direction substantially perpendicular to the longitudinal direction of the guide rod.

According to yet another illustrative embodiment, an impaction tool for impacting bone material comprises a handle portion and a plate. The plate has a first dimension in a length direction extending from a first end of the plate proximate the handle portion to a second end of the plate distal of the handle portion. The plate has a second dimension in a breadth direction being substantially perpendicular to the length direction. The first dimension is greater than the second dimension and the plate is curved in the breadth direction.

According to yet another embodiment, a method of impacting bone material comprises providing an impaction apparatus comprising an impaction tool and a guide element. The guide element has a central bore and provides a predetermined distance between the central bore and the impaction tool in a direction substantially perpendicular to a longitudinal direction of the central bore. The medical device is inserted into a bone of a patient. A guide rod is fixed to the medical device. The guide rod is inserted into the central bore of the guide element. The bone material is inserted into a cavity in the bone. The impaction apparatus is moved along the guide rod to impact the bone material.

According to yet another embodiment, a modular system for providing a hip joint endoprosthesis comprises a stem, a prosthetic head, a sleeve, a guide rod and an apparatus for impacting bone material. The stem is insertable into a femur of a patient and comprises a male cone. The prosthetic head comprises a female cone connectable to the male cone. The sleeve comprises a female cone connectable to the male cone and has a central bore. The guide rod is connectable to the stem and insertable into the central bore of the sleeve. The apparatus for impacting bone material comprises a guide element movable along the guide rod in a longitudinal direction of the guide rod and an impaction tool connected to the guide element.

BRIEF DESCRIPTION OF THE DRAWINGS

Further embodiments of the present subject matter are defined in the appended claims and will become more apparent with the following detailed description when taken with reference to the accompanying drawings, in which:

FIG. 1b shows a schematic cross-sectional view of the apparatus for impacting bone material shown in FIG. 1a;

DETAILED DESCRIPTION

Figure 1A:
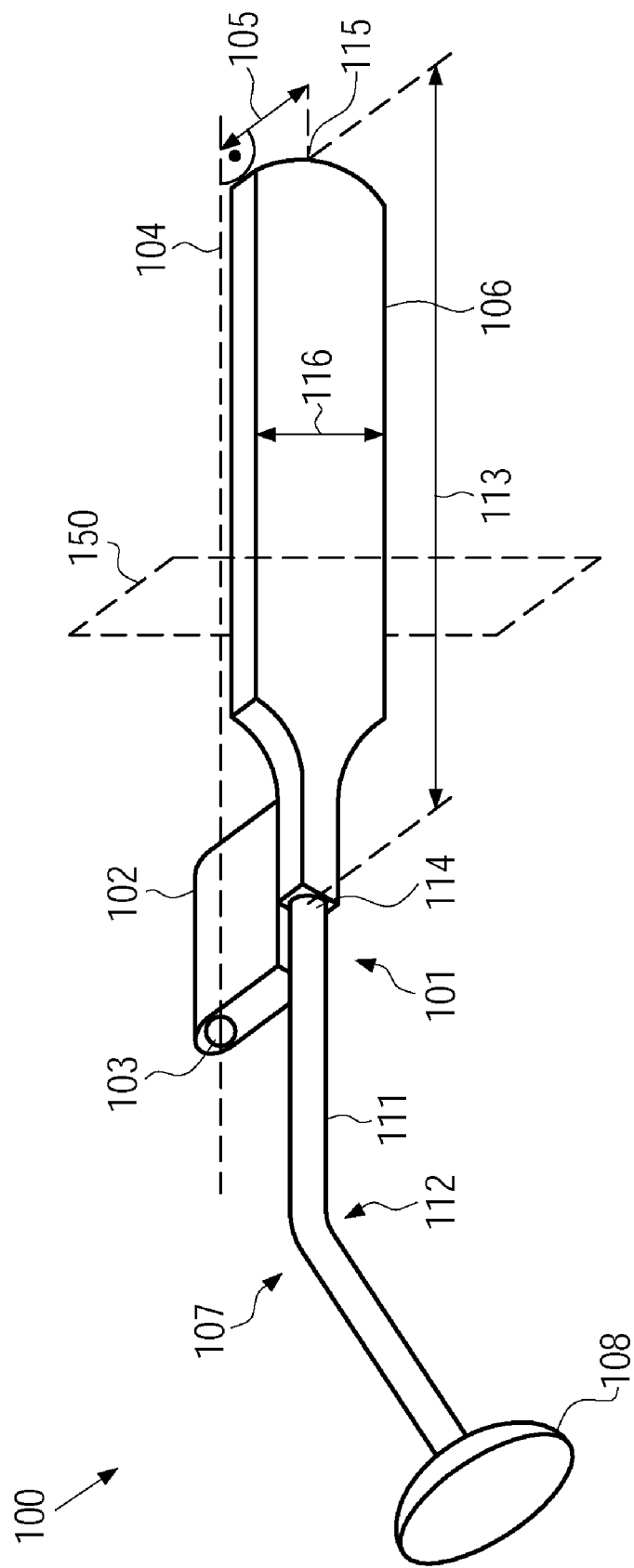
FIG. 1a shows a schematic perspective view of an apparatus for impacting bone material according to an embodiment of the present subject matter.

While the present subject matter is described with reference to the embodiments as illustrated in the following detailed description as well as in the drawings, it should be understood that the following detailed description as well as the drawings are not intended to limit the present subject matter to the particular embodiments disclosed, but rather the described embodiments merely exemplify the various aspects of the present subject matter, the scope of which is defined by the appended claims.

According to one embodiment, an apparatus for impacting bone material comprises an impaction tool and a guide element which are connected with each other. The guide element may be movable along a guide rod, which can be fixed to a medical device that is inserted into a bone of a patient.

The guide element may, in some embodiments, have a bore, wherein the guide rod may be inserted into the bore. Hence, the apparatus may slide along the guide rod, a longitudinal axis of the impaction tool being maintained substantially parallel to a longitudinal direction of the guide rod.

The impaction tool can be provided at a predetermined distance to the bore in a direction substantially perpendicular to the longitudinal axis of the bore. Hence, if the apparatus is moved along the guide rod, the impaction tool can be maintained substantially at the predetermined distance to the guide rod while being moved back and forth along the guide rod.

In some embodiments, the medical device to which the guide rod is connected may comprise a component of a hip joint endoprosthesis, for example a stem which is inserted into the femur of a patient. The present subject matter, however, is not restricted to embodiments wherein the medical device comprises a stem. In other embodiments, the guide rod may be connected to a prosthetic head of a hip joint endoprosthesis, or may be connected to an endoprosthesis other than a hip joint endoprosthesis, for example to a knee endoprosthesis. In still further embodiments, the guide rod can be connected to a medical device other than an endoprosthesis, for example to a bone nail.

The guide rod may be fixed to the medical device before or after inserting the medical device into the patient's bone. In some embodiments, the guide rod may comprise a thread, for example an external thread, and a corresponding thread, for example an internal thread, may be provided in the medical device. In such embodiments, the guide rod can be screwed into the medical device.

Thereafter, the guide rod can be inserted into the central bore of the guide element. Bone material such as bone grafts obtained from the patient or from another person can be inserted into a cavity in the bone, for example into a gap between the medical device and the bone. In embodiments wherein the medical device comprises a stem insertable into a long bone, for example the femur, of the patient, the gap between the stem and the bone may comprise metaphyseal defects occurring, for example, in the context of hip joint endoprosthesis loosening. To impact the bone material, the apparatus can be moved back and forth along the guide rod. Thereby, the impaction tool may push the bone material into the cavity and may compress the bone material.

Since the impaction tool is provided at the predetermined distance to the bore of the guide element in a direction substantially perpendicular to the longitudinal axis of the bore, the impaction tool is radially spaced apart from the guide rod by a distance being substantially equal to the predetermined distance. This may allow the impaction tool to pass laterally to the medical device. Moreover, the impaction tool may enter the cavity in the bone in a direction substantially parallel to the direction of the guide rod. Hence, the impaction tool may be precisely guided into the cavity. This may allow an efficient compacting of the bone material in the cavity, and may simplify the compaction of the bone material compared to a free-hand operation of the impaction tool.

In some embodiments, the impaction tool may comprise a handle portion and a plate. The plate may have a first dimension in a length direction extending from a first end of the plate proximate the handle portion to a second end of the plate distal of the handle portion, and a second dimension in a breadth direction being substantially perpendicular to the length direction. The first dimension can be greater than the second dimension. Additionally, the plate may be curved in the breadth direction. Thus, the plate may have an oblong, curved configuration.

The oblong, curved configuration may simplify an insertion of the impaction tool into a gap between a medical device having a curved surface such as, for example, a substantially cylindrical stem of a hip joint endoprosthesis, and a bone of the patient Moreover, an efficient impaction of the bone material in the vicinity of the medical device can be obtained.

In some embodiments wherein the medical device comprises a stem of a hip joint endoprosthesis, the stem may comprise a male cone for attachment of a prosthetic head comprising a female cone. The male cone and the female cone provide a conical connector for connecting the stem and the prosthetic head with each other.

In some of these embodiments, the insertion of bone material into the gap between the stem and the patient's femur and the impaction of the bone material by means of the above-described impaction apparatus can be performed before the connection of the stem and the prosthetic head. To protect the male cone from mechanical damage and/or contamination during the impaction, a sleeve may be attached to the male cone of the stem during the impaction.

The sleeve may comprise a female cone connectable to the male cone such that the sleeve may be connected to the stem by means of a conical connection. Additionally, the sleeve may comprise a central bore. To fix the guide rod to the stem, the guide rod may be inserted into the central bore of the sleeve, and may be connected to a connection element provided in the stem. For example, the guide rod can be screwed to a thread provided in the stem.

In some embodiments, the sleeve may have a substantially cylindrical outer surface, wherein a radius of the outer surface may be approximately equal to a radius of the stem. Thus, during the impaction of the bone material, the impaction tool may pass laterally to the sleeve and the stem.

Further embodiments of the present subject matter will be described with reference to FIGS. 1a and 1b.

FIG. 1a shows a schematic perspective view of an apparatus 100 for impacting bone material according to one embodiment. A schematic cross-sectional view of the apparatus 100 along a plane 150 is shown in FIG. 1b.

The apparatus 100 comprises an impaction tool 101 and a guide element 102. The guide element 102 comprises a bore 103 extending through the guide element 102. The bore 103 may have a substantially cylindrical shape. In FIGS. 1a and 1b, reference numeral 104 denotes a longitudinal axis of the bore 103.

The impaction tool 101 is connected to the guide element 102. In some embodiments, the impaction tool 101 and the guide element 102 can be integral. In other embodiments, the impaction tool 101 and the guide element 102 may be connected by means of welding, screwing, gluing or any other connection technique known to persons skilled in the art.

The guide element 102 may act as a spacer, spacing the impaction tool 105 apart from the bore 103. In FIGS. 1a and 1b, reference numeral 105 denotes a distance between the longitudinal axis 104 of the bore 103 and the impaction tool 101, measured in a direction substantially perpendicular to the longitudinal axis 104.

The impaction tool 101 comprises a plate 106 and a handle portion 107.

In some embodiments, the plate 106 can be curved around the longitudinal axis 104 of the bore 103. In such embodiments, a first surface 109 and a second surface 110 (FIG. 1b) of the plate 106 may be substantially cylindrical. The first surface 109 is facing the longitudinal axis 104 of the bore 103, and the second surface 110 is opposite the longitudinal axis 104.

A cylinder axis of the first surface 109 and a cylinder axis of the second surface 110 can be substantially parallel to the longitudinal axis of the bore 104. Hence, in case the apparatus 100 is moved in a direction parallel to the longitudinal axis 104, the first surface 109 and/or the second surface 110 may move along an object whose surface comprises at least a portion having a cylindrical shape with an axis substantially parallel to the longitudinal axis 104 such as, for example, a sleeve 203, a stem 202 of a hip joint endoprosthesis, and/or a prosthetic head 301 of a hip joint endoprosthesis (FIGS. 2a, 2b and 3), as will be explained in more detail below.

In some embodiments, the first surface 109 and the second surface 110 can be substantially concentric around the longitudinal axis 104 of the bore 103. In such embodiments, the cylinder axis of the first surface 109 and the cylinder axis of the second surface 110 substantially coincide with the longitudinal axis 104. A radius of the first surface 109 may be approximately equal to the distance 105 between the longitudinal axis 104 and the first surface 109, and a radius of the second surface 110 may be approximately equal to a sum of the distance 105 and a thickness of the plate 106. In some embodiments, the second surface 110 may have a radius of about 13 mm, a radius of about 15 mm or a radius of about 18 mm.

In such embodiments, in case the apparatus 100 is rotated around the longitudinal axis 104 of the bore 103, the plate 106 may move along the sleeve 203, the stem 203 and/or the prosthetic head 301.

In some embodiments, the distance 105 between the longitudinal axis 104 of the bore 103 and the impaction tool 104 may have a value in a range from about 10 mm to about 22 mm, for example a value of about 10.5 mm, corresponding to a typical thickness of a stem of a hip joint endoprosthesis according to the state of the art.

The present subject matter is not restricted to embodiments wherein the first surface 109 and the second surface 110 are substantially cylindrical. In other embodiments, the plate 106 may have a substantially flat configuration. In such embodiments, the first surface 109 and the second surface 110 may be substantially planar and parallel to each other.

In FIG. 1a, reference numeral 113 denotes a first dimension of the plate 106 in a length direction, and reference numeral 116 denotes a second dimension of the plate 106 in a breadth direction of the plate 106. The length direction runs from a first end 114 of the plate 106 proximate the handle portion 107 to a second end 115 of the plate 106 distal of the handle portion 107. Hence, the length direction of the plate 106 may be substantially parallel to the longitudinal axis 104 of the bore 103 and the breadth direction of the plate 106 can be substantially perpendicular to the longitudinal axis 104.

The first dimension 113 may be greater than the second dimension 116. Thus, the plate 106 obtains an oblong configuration. This may facilitate an insertion of the plate 106 of the apparatus 100 into a relatively long and narrow cavity formed in a bone of the patient, for example into a gap between the patient's femur and the stem 202 of a hip joint endoprosthesis.

In one embodiment, the first dimension 113 may have a value in a range from about 20 mm to about 120 mm, in particular a value of about 70 mm, and the second dimension 116 may have a value in a range from about 12 mm to about 25 mm, in particular a value of about 16 mm, a value of about 19 mm or a value of about 22 mm.

The handle portion 107 may comprise a rod 111 connected to the plate 106 and/or the guide element 102. At an end of the rod 111 distal of the plate 106, a knob 108 may be provided. In the operation of the apparatus 100, a person may hold the handle portion 107 of the impaction tool 101 to move the apparatus 100. The presence of the knob 108 may make it relatively easy to exhibit a force on the apparatus acting substantially in the longitudinal axis 104 of the bore 103.

In some embodiments, the rod 111 may comprise a kink 112, such that the rod 111 is bent away from the guide element 102. This may simplify the operation of the apparatus 100, since the bent configuration of the rod 111 may allow a person operating the apparatus to provide his or her hand at a distance to the guide element 102 when holding the knob 108. As will be explained in more detail below with respect to FIGS. 2 and 3, in the operation of the apparatus 100, a guide rod 201 may be inserted into the bore 103 of the guide element 102. The kink 112 may help to reduce a likelihood that the hand of the person operating the apparatus 100 abuts the guide rod 201.

Figure 2A:
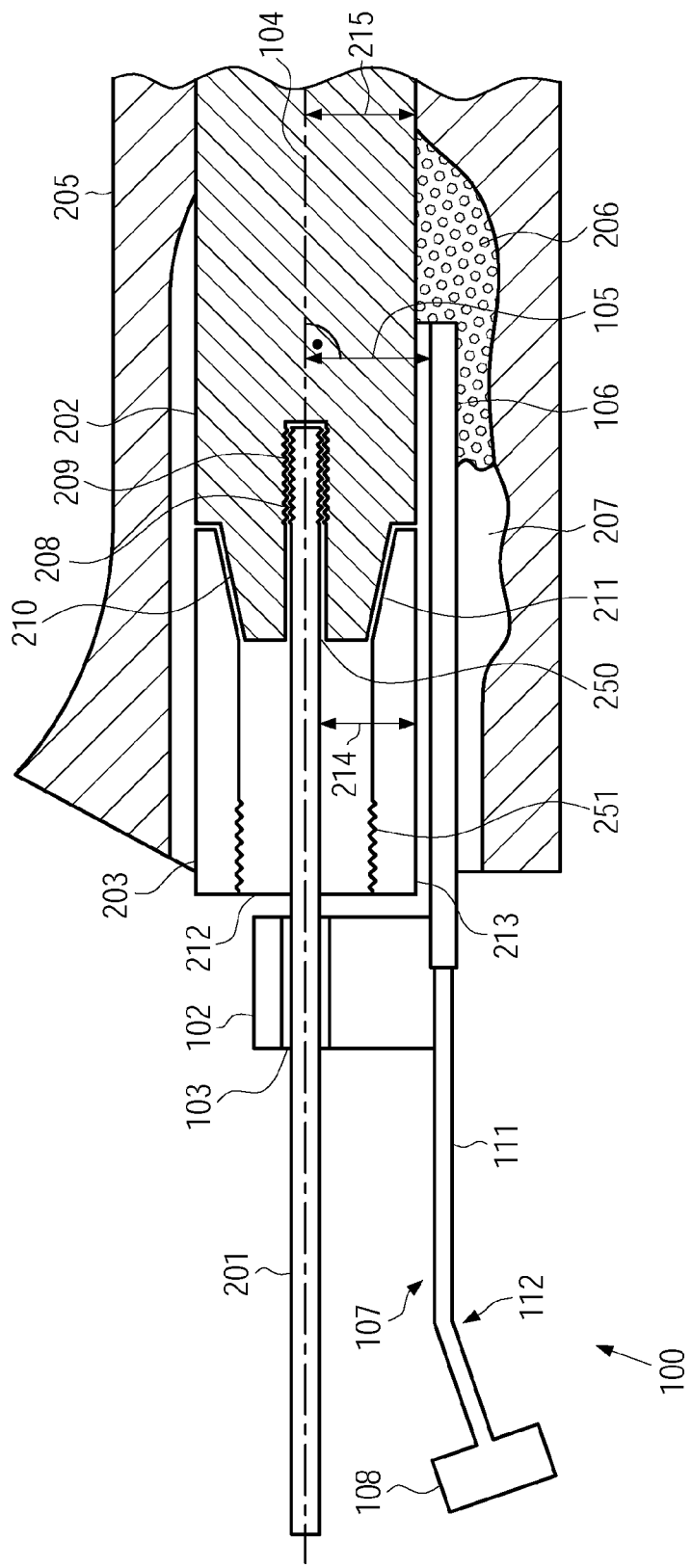
FIGS. 2a and 2b show schematic cross-sectional views of a femur of a patient in stages of a method according to an embodiment of the present subject matter.
Figure 2B:
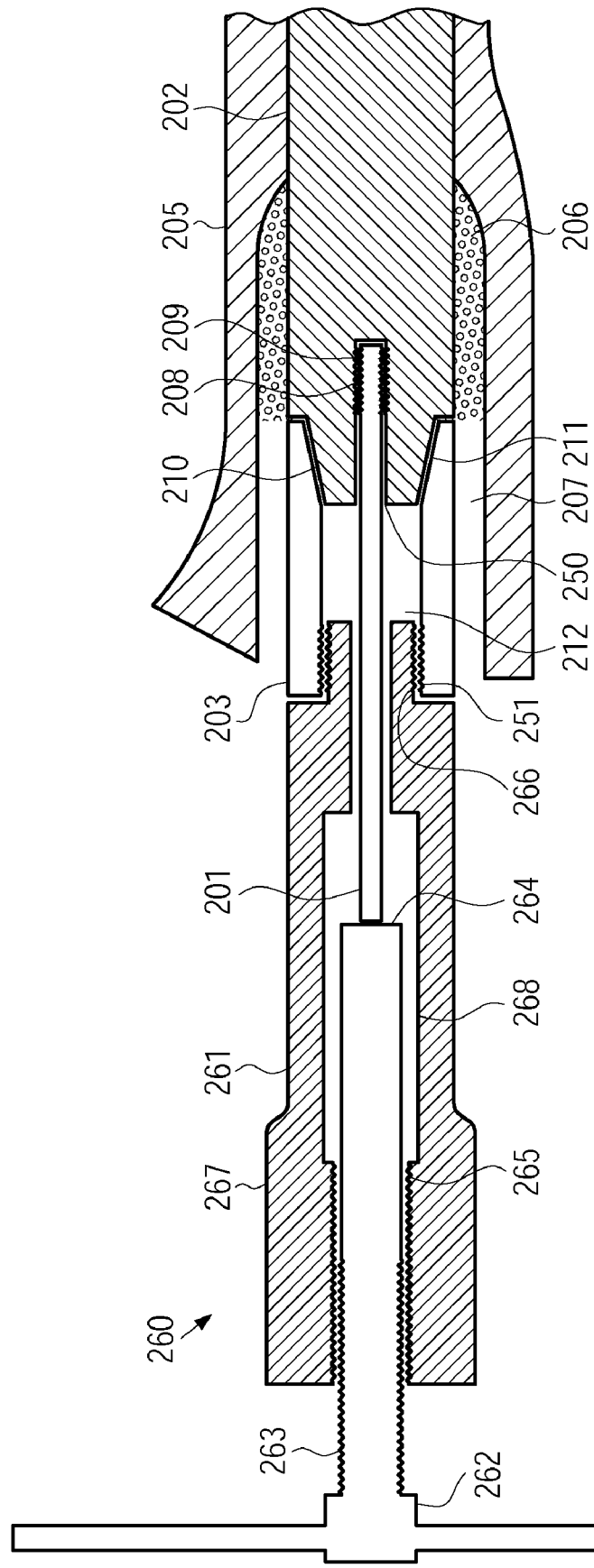

In the following, a method of implanting a hip joint endoprosthesis wherein bone material is impacted by means of a method according to the present subject matter will be described with reference to FIGS. 2a and 2b. FIG. 2a shows a schematic cross-sectional view of a femur 205 of a patient in a first stage of the implantation of the hip joint endoprosthesis. FIG. 2b shows a schematic cross-sectional view of the femur 205 in a later stage of the implantation process.

Figure 3:
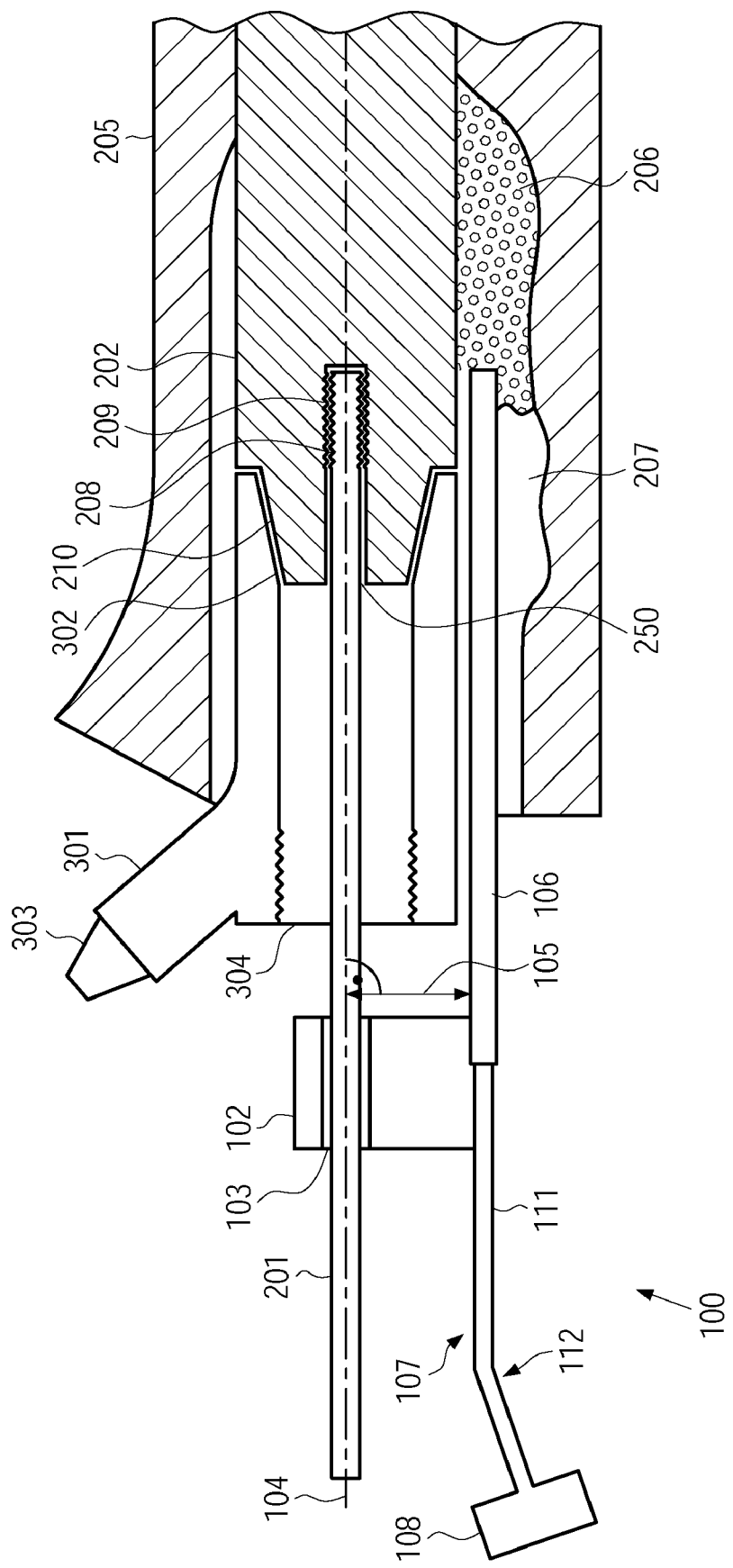
FIG. 3 shows a schematic cross-sectional view of a femur of a patient in a stage of a method according to another embodiment of the present subject matter.

The hip joint endoprosthesis comprises a stem 202 which is insertable into the femur 205. The stem 202 is an example of a medical device insertable into a bone of a patient. The hip joint endoprosthesis may additionally comprise a prosthetic head 301 which is shown in FIG. 3. Furthermore, the hip joint endoprosthesis may comprise an artificial joint ball (not shown) which can be attached to the prosthetic head 301, and which may be inserted into an artificial joint socket (not shown) that can be attached to the patient's pelvic bone.

The stem 202 may comprise a male cone 210. The stem 202 may further comprise a bore 250 extending through the male cone 210. An internal thread 209 can be provided in the bore 250.

The prosthetic head 301 may comprise a female cone 302. The female cone 302 may have a cone angle substantially equal to the cone angle of the male cone 210, and may have an internal diameter corresponding to the external diameter of the male cone 210. Thus, the male cone 210 and the female cone 302 provide a cone connection configured for connecting the stem 202 and the prosthetic head 301.

The prosthetic head 301 may further be adapted for connection of a joint ball (not shown) to the prosthetic head. To this end, the prosthetic head 301 may comprise a male cone 303 adapted to provide a cone connection between the prosthetic head 301 and the joint ball.

In some embodiments, the hip joint endoprosthesis may be specifically adapted for use as a revision endoprosthesis which may be implanted into a patient after removal of an endoprosthesis. To this end, the stem 202 can be configured to provide a diaphyseal anchorage and bridging of damaged metaphyseal bone by means of a diaphyseal press fit, similar to the stem of the prosthesis described in DE 43 20 086 A1, in Wirtz D C, Heller K-D, Holzwarth U, Siebert C, Pitto R P, Zeiler G, Blencke B A, Forst R: A modular femoral implant for uncemented stem revision in THR. International Orthopaedics (SICOT) 2000 24: 134-138, in particular in the section "Materials and methods", FIGS. 1 and 2, in M. Schramm, D. C. Wirtz, U. Holzwarth and R. P. Pitto: The Morse Taper Junction in Modular Revision Hip Replacement—A Biomechanical and Retrieval Analysis. Biomedizinische Technik 45 (2000), 105-109 or in Mumme T, Mueller-Rath R, Weisskopf M, Andereya S, Neuss M, Wirtz D C: The cement-free modular revision prosthesis MRP-Titanium in clinical follow-up. Z Orthop. 2004; 142:314-321, in particular in the section "Material und Methodik" and in FIG. 1, which are incorporated herein by reference. The prosthetic head 301 and further components of the hip joint endoprosthesis may also have features as described in the above references.

In the implantation of the hip joint endoprosthesis, first a primary hip joint endoprosthesis or, alternatively, the natural hip joint of the patient may be removed. If the primary hip joint endoprosthesis was connected to the femur by means of bone cement, residual cement may be removed using chisels and/or cutters known to persons skilled in the art.

Thereafter, the stem 202 may be inserted into the patient's femur 205 using tools known to persons skilled in the art.

In some embodiments, length, size and shape of the stem 202, which may be determined in advance using x-ray images of the patient, may be confirmed using a trial prosthesis, which may be inserted before the insertion of the stem 201. The trial prosthesis may comprise a stem and a prosthetic head having dimensions approximately equal to those of the stem 202 and the prosthetic head 301. The trial prosthesis may have a substantially smooth surface, whereas the stem 202 and the prosthetic head 301 may have a rough surface having a roughness Rz of approximately 50 µm for facilitating bone engraftment. Moreover, the trial prosthesis may comprise a different material than the stem 202 and the prosthetic head 301, which may comprise an implant material such as, for example, a titanium alloy. The trial prosthesis need not comprise an implant material. The stem of the trial prosthesis may be inserted into the femur 205, and the prosthetic head of the trial prosthesis can be connected to the stem of the trial prosthesis. Subsequently, a correct fit of the trial prosthesis may be investigated using methods well known to persons skilled in the art. Then, the trial prosthesis may be removed.

After the insertion of the stem 202, bone material 206 which may, for example, comprise bone grafts or chips can be inserted into a gap 207 between the stem 202 and the femur 205. As persons skilled in the art know, the gap 207 may be caused, for example, by metaphyseal bone defects such as osteolysis. The bone material 206 may comprise autogenous bone material obtained from a donor site of the patient, or allogenic material obtained from a foreign bone. Before inserting the bone material 206 into the gap 207, the bone material 206 may be milled using a bone mill of a type well known to persons skilled in the art.

After insertion of the bone material 206, the bone material 206 may be impacted. To this end, a guide rod 201 which is connectable to the stem 202 may be used in combination with the apparatus 100 for impacting bone material described above, as will be explained in the following.

The guide rod 201 can be connected to the stem 202 by screwing an external thread 208 provided at an end of the guide rod 201 to an internal thread 209 provided in the bore 250 of the stem 202. The present subject matter, however, is not restricted to embodiments wherein the guide rod 201 is screwed to the stem 202. In other embodiments, the guide rod 201 may, for example, be connected to the stem 202 by means of a cone connection.

The guide rod 201 need not be connected to the stem 202 immediately before the impaction of the bone material 206. In some embodiments, the guide rod 201 may be employed for purposes other than guiding the apparatus 100, for example for guiding a known instrument for insertion of the stem 202. In such embodiments, the guide rod 201 can be connected to the stem 202 before inserting the stem 202 into the femur 205, and may remain connected to the stem 205 after removing the instrument for insertion of the stem 202.

In other embodiments, the guide rod 201 may be connected to the stem 202 immediately before impacting the bone material 206.

The guide rod 201 may have a substantially cylindrical shape, and may be adapted for insertion into the bore 103 of the guide element of the apparatus 100. For this purpose, the diameter of the guide rod may be slightly smaller than the diameter of the bore 103. Thus, the longitudinal axis 104 of the bore 103 and, hence, the impaction tool 101 connected to the guide element 102 wherein the bore 103 is provided, may be aligned to the guide rod 201 such that the apparatus 100 is guided by the guide rod 201. The guide rod 201 may allow a motion of the apparatus 100 in a direction substantially parallel to and along the guide rod 201, and may also allow a rotation of the apparatus 101 around the guide rod 201.

In some embodiments, a sleeve 203 can be connected to the stem 202 before impacting the bone material 206 to protect the male cone 210 of the stem 202 during the impaction of the bone material 206.

The sleeve 203 may comprise a female cone 211 adapted such that a cone connection may be established between the male cone 210 of the stem 202 and the female cone 211 of the sleeve 203. The cone connection may allow a quick connection of the sleeve 203 and the stem 202, and the presence of the female cone 211 on the male cone 210 may protect the male cone 210 from adverse influences such as scratching and/or contamination.

The sleeve 203 may have a substantially cylindrical outer surface 213. In particular, a portion of the outer surface 213 of the sleeve 203 distal of the female cone 211 may be substantially cylindrical. A radius 214 of the outer surface 213 of the sleeve 203 may be approximately equal to a radius 215 of the stem 202. Hence, the outer surface 213 of the sleeve 203 may smoothly adjoin the stem 202. The sleeve 203 may further comprise a central bore 212 having a diameter greater than the diameter of the guide rod 201. Thus, the guide rod 201 may be inserted into the central bore of the sleeve 203 as the sleeve 203 is connected to the stem 202. In the central bore 212 of the sleeve 203, an internal thread 251 may be provided. As will be explained in more detail below, the internal thread 251 may be used to apply a dismantling instrument 260 (FIG. 2b) for removing the sleeve 203 after the impaction of the bone material 260.

In some embodiments, the bone material 206 may be filled into the gap 207 after connecting the sleeve 203 to the stem 202. Thus, a contamination of the male cone 210 with the bone material can be reduced.

After connecting the sleeve 203 to the stem 202, the guide rod 201 can be inserted into the bore 103 of the guide element 102 of the apparatus 100. Then, the apparatus 100 may be moved back and forth along the guide rod 201 to compact the bone material 206. This can be done manually by a person holding the handle portion 107 of the impaction tool 101 in his or her hand. As the apparatus 100 is moved towards the stem 202, the plate 106 of the apparatus 100 may enter the gap 207 between the femur 205 and the stem 202 and/or the sleeve 203, moving in a direction substantially parallel to the longitudinal axis 104 of the bore 103 due to the guidance provided by the guide rod 201. Since the distance 105 between the longitudinal axis 104 and the impaction tool 101 may be greater than the radius 214 of the sleeve 203 and the radius 215 of the stem 202, the plate 106 may move along the outer surface 213 of the sleeve 203 and along the stem 202. The second end 115 of the plate 206 which is distal of the handle portion 117 may push the bone material 206 into the gap 207 between the stem 202 and the femur 205, and may also compress the bone material 206. Thus, the bone material 206 may be impacted.

In addition to moving the apparatus 100 back and forth along the guide rod 201, the apparatus 100 may also be rotated around the guide rod 201. Thus, portions of the bone material 206 on different sides of the stem 202 may be compressed. Additionally, a rotational motion of the apparatus 100 may allow moving and compressing the bone material 206 in circumferential direction of the stem 202. This may allow substantially completely filling the gap 207 with relatively dense bone material 206, as shown in FIG. 2b.

FIG. 2b shows a schematic cross-sectional view of the femur 205 in a later stage of the method of inserting a hip joint endoprosthesis.

After impacting the bone material 206, the apparatus 100 may be removed by withdrawing the guide rod 201 from the bore 130. Then, the sleeve 203 may be removed from the stem 202. To remove the sleeve 203, a dismantling instrument 260 may be used.

The dismantling instrument 260 comprises a hollow bar 261 and an impression rod 264. The hollow bar 261 comprises a central bore 268 which extends longitudinally through the hollow bar 261. At a first end of the hollow bar 261, an external thread 266 is provided. The external thread 266 may correspond to the internal thread 251 of the sleeve 203 such that the hollow bar 261 can be screwed into the sleeve 203 for providing a connection between the hollow bar 261 and the sleeve 203.

The central bore 268 comprises an internal thread 265 located at a second end of the hollow bar 261. The impression rod 264 comprises an external thread 263 corresponding internal thread 265 such that the impression rod 264 can be screwed into the hollow bar 261. Additionally, the impression rod 264 comprises a handle portion 262.

In some embodiments, a grip portion 267 can be provided at the second end of the hollow bar 261. The grip portion 267 may have a greater diameter than the rest of the hollow bar 261 and can comprise a textured surface.

To remove the sleeve 203, the guide rod 201 may be inserted into the central bore 268 of the hollow bar 261. Thereafter, the hollow bar 261 can be screwed into the sleeve 203. Thus, the hollow bar 261 and the sleeve 203 are connected with each other. The guide rod 201 extends into the central bore 268 of the hollow bar 261. Subsequently, the impression rod 264 can be screwed into the hollow bar 261.

For this purpose, an operator may hold the grip portion 267 of the hollow bar 261 and the handle portion 262 of the impression rod 264, rotating the impression rod 264 around its longitudinal axis.

As the impression rod 264 is screwed into the hollow bar 261, an end of the impression rod 264 approaches the guide rod 201 until it touches the guide rod 201. If the impression rod 264 is screwed further into the hollow bar 261, the impression rod 264 exhibits a force on the guide rod 201, pushing the guide rod 201 towards the stem 202. Thereby, a counterforce pulling the hollow bar 261 and the sleeve 203 connected thereto away from the stem 203 is obtained, which may disconnect the cone connection between the sleeve 203 and the stem 202.

After the removal of the sleeve 203, the prosthetic head 301 may be connected to the stem 202 by means of the cone connection provided by the male cone 210 of the stem 202 and the female cone 302 of the prosthetic head 301. Subsequently, the guide rod 201 may be removed, and a screw (not shown) may be inserted into the bore 250 of the stem through the central bore 304 of the prosthetic head 301 and screwed to the internal thread 209 of the stem 202 for securing the prosthetic head 301 to the stem 202.

Thereafter, a joint ball (not shown) may be connected to the male cone 303 of the prosthetic head 301, and the joint ball may be inserted into an artificial joint socket attached to the patient's pelvic bone or, alternatively, into the natural joint socket of the patient.

The present subject matter is not restricted to embodiments wherein the sleeve 203 is connected to the stem 202 during the impaction of the bone material 206. In other embodiments, the prosthetic head 301 can be connected to the stem 202 before impacting the bone material 206 by means of the apparatus 100.

FIG. 3 shows a schematic cross-sectional view of the femur 205 during the impaction of the bone material in such an embodiment. For convenience, in FIG. 3 and in FIGS. 1a to 2b, like reference numerals have been used to denote like components. The guide rod 201 extends through the central bore 304 of the prosthetic head 301 and is inserted into the bore 103 of the guide element 103 of the apparatus 100. The apparatus 100 can be moved back and forth along the guide rod 201, and may optionally be rotated around the guide rod 201 to push the bone material 206 into the gap 207 between the stem 202 and the femur 205. Thereby, the plate 106 of the apparatus 100 may move along the prosthetic head 301 and the stem 201.

In still further embodiments, neither the sleeve 203 nor the prosthetic head 301 is connected to the stem 202 during the impaction of the bone material 206.

Further modifications and variations of the present subject matter will be apparent to those skilled in the art in view of this description. Accordingly, this description is to be construed as illustrative only and is for the purpose of teaching those skilled in the art the general manner of carrying out the present subject matter. It is to be understood that the forms of the present subject matter shown and described herein are to be taken as the presently preferred embodiments.

The invention claimed is:

1. A modular system for providing a hip joint endoprosthesis, comprising:
 a stem insertable into a femur of a patient, said stem comprising a male cone;
 a prosthetic head comprising a female cone connectable to said male cone;

a sleeve comprising a female cone connectable to said male cone and having a central bore;

a guide rod connectable to said stem and insertable into said central bore of said sleeve; and an apparatus for impacting bone material comprising a guide element movable along said guide rod in a longitudinal direction of said guide rod and an impaction tool connected to said guide element;

wherein said guide element is adapted to provide a predetermined distance between said guide rod and said impaction tool, said predetermined distance being greater than a radius of said sleeve and a radius of said stem to allow motion of said impaction tool along said sleeve and said stem.

2. A modular system according to claim 1, wherein said sleeve comprises a substantially cylindrical outer surface.

3. A modular system according to claim 2, wherein a radius of said outer surface is approximately equal to a radius of said stem.

4. A modular system according to claim 1, wherein the guide element is adapted to act as a spacer, spacing the impaction tool apart from the bore.

5. A modular system according to claim 1, wherein the guide element and the impaction tool are integral.

6. A modular system according to claim 1, wherein the guide element and the impaction tool are connected by means of at least one of welding, screwing and gluing.

7. A modular system according to claim 1, wherein the impaction tool is provided outside said bore.

8. A modular system according to claim 1 wherein said guide element has a bore, said bore having a longitudinal axis;
said impaction tool being provided at a predetermined distance to said bore in a direction substantially perpendicular to said longitudinal axis of said bore.

9. A modular system according to claim 1 wherein said impaction tool comprises:
a plate being curved around said longitudinal axis of said bore; and
a handle portion connected to said plate.

10. A modular system according to claim 9 wherein said plate comprises a first substantially cylindrical surface and a second substantially cylindrical surface, said first and second substantially cylindrical surface being substantially concentric around said longitudinal axis of said bore.

11. A modular system according to claim 10 wherein said first substantially cylindrical surface is distal from said guide element, and wherein a radius of curvature of said first substantially cylindrical surface is in a range from about 10 mm to about 22 mm.

12. A modular system according to claim 9 wherein said handle portion comprises a rod connected to said plate and a knob provided at an end of said rod distal of said plate.

13. A modular system according to claim 12 wherein said rod comprises a kink.

14. A modular system according to claim 1 wherein said guide element is rotatable around said guide rod.

15. A modular system according to claim 1 wherein said guide rod has a substantially cylindrical shape and wherein said guide element comprises a bore adapted for insertion of said guide rod.

16. A modular system according to claim 1 wherein said impaction tool comprises:
a handle portion comprising a bent bar and a knob provided at an end of said bent bar; and
a plate having a first dimension in a length direction extending from a first end of said plate proximate said handle portion to a second end of said plate distal of said handle portion and a second dimension in a breadth direction being substantially perpendicular to said length direction, said first dimension being greater than said second dimension;
wherein said plate is curved in said breadth direction.

17. A modular system according to claim 16 wherein said plate comprises a first substantially cylindrical surface and a second substantially cylindrical surface, said first substantially cylindrical surface and said second substantially cylindrical surface being substantially concentric.

18. A modular system for providing a hip joint endoprosthesis, comprising:
a stem insertable into a femur of a patient said stem comprising a male cone;
a prosthetic head comprising a female cone connectable to said male cone;
a sleeve comprising a female cone connectable to said male cone and having a central bore;
a guide rod connectable to said stem and insertable into said central bore of said sleeve; and
an apparatus for impacting bone material comprising a guide element movable along said guide rod in a longitudinal direction of said guide rod and an impaction tool connected to said guide element,
wherein said central bore of said sleeve comprises an internal thread, said system further comprising a dismantling instrument comprising:
a hollow bar comprising an external thread provided at a first end of said hollow bar, said external thread being screwable into said internal thread of said sleeve, said hollow bar further comprising a central bore longitudinally extending therethrough, an internal thread being provided in said central bore at a second end of said hollow stem, said guide rod being insertable into said central bore when connected to said stem; and
an impression rod insertable into said central bore of said hollow bar and comprising an external thread screwable into said internal thread of said hollow bar for exhibiting a force on said guide rod when connected to said stem and inserted into said central bore of said hollow bar.

19. A modular system according to claim 18, wherein said guide element has a bore, said bore having a longitudinal axis;
said impaction tool being provided at a predetermined distance to said bore in a directionsubstantially perpendicular to said longitudinal axis of said bore.

20. A modular system according to claim 19 wherein said impaction tool comprises:
a plate being curved around said longitudinal axis of said bore; and
a handle portion connected to said plate.

21. A modular system according to claim 20 wherein said plate comprises a first substantially cylindrical surface and a second substantially cylindrical surface, said first and second substantially cylindrical surface being substantially concentric around said longitudinal axis of said bore.

22. A modular system according to claim 21 wherein said first substantially cylindrical surface is distal from said guide element, and wherein a radius of curvature of said first substantially cylindrical surface is in a range from about 10 mm to about 22 mm.

23. A modular system according to claim 20 wherein said handle portion comprises a rod connected to said plate and a knob provided at an end of said rod distal of said plate.

24. A modular system according to claim 23 wherein said rod comprises a kink.

25. A modular system according to claim 18 wherein said guide element is rotatable around said guide rod.

26. A modular system according to claim 18 wherein said guide rod has a substantially cylindrical shape and wherein said guide element comprises a bore adapted for insertion of said guide rod.

27. A modular system according to claim 18 wherein said impaction tool comprises:
   a handle portion comprising a bent bar and a knob provided at an end of said bent bar; and
   a plate having a first dimension in a length direction extending from a first end of said plate proximate said handle portion to a second end of said plate distal of said handle portion and a second dimension in a breadth direction being substantially perpendicular to said length direction, said first dimension being greater than said second dimension;
   wherein said plate is curved in said breadth direction.

28. A modular system according to claim 27 said plate comprises a first substantially cylindrical surface and a second substantially cylindrical surface, said first substantially cylindrical surface and said second substantially cylindrical surface being substantially concentric.

29. A modular system according to claim 18 wherein said sleeve comprises a substantially cylindrical outer surface.

30. A modular system according to claim 29 wherein a radius of said outer surface is approximately equal to a radius of said stem.

31. A modular system according to claim 18 wherein said guide element is adapted to provide a predetermined distance between said guide rod and said impaction tool, said predetermined distance being greater than a radius of said sleeve and a radius of said stem to allow motion of said impaction tool along said sleeve and said stem.

32. A modular system according to claim 19 wherein the guide element is adapted to act as a spacer, spacing the impaction tool apart from the bore.

33. A modular system according to claim 19 wherein the guide element and the impaction tool are integral.

34. A modular system according to claim 19 wherein the guide element and the impaction tool are connected by means of at least one of welding, screwing and gluing.

35. A modular system according to claim 19 wherein the impaction tool is provided outside said bore.

* * * * *